(12) United States Patent
Shuros et al.

(10) Patent No.: US 10,639,097 B2
(45) Date of Patent: May 5, 2020

(54) CHRONICALLY IMPLANTABLE MEDICAL DEVICES CONFIGURED FOR EXTRACTION AND EXTRACTION DEVICES FOR EXTRACTING CHRONICALLY IMPLANTED MEDICAL DEVICES

(71) Applicant: CARDIAC PACEMAKERS, INC., St. Paul, MN (US)

(72) Inventors: Allan Charles Shuros, St. Paul, MN (US); Arjun D. Sharma, St. Paul, MN (US); Brian Soltis, St Paul, MN (US)

(73) Assignee: CARDIAC PACEMAKERS, INC., St. Paul, MN (US)

(\*) Notice: Subject to any disclaimer, the term of this patent is extended or adjusted under 35 U.S.C. 154(b) by 513 days.

(21) Appl. No.: 15/474,899

(22) Filed: Mar. 30, 2017

(65) Prior Publication Data
US 2017/0281261 A1  Oct. 5, 2017

Related U.S. Application Data

(60) Provisional application No. 62/397,915, filed on Sep. 21, 2016, provisional application No. 62/316,074, filed on Mar. 31, 2016.

(51) Int. Cl.
*A61B 18/14* (2006.01)
*A61N 1/05* (2006.01)
(Continued)

(52) U.S. Cl.
CPC ........ *A61B 18/148* (2013.01); *A61B 17/3209* (2013.01); *A61B 17/320016* (2013.01);
(Continued)

(58) Field of Classification Search
CPC .............. A61B 18/148; A61B 18/1445; A61B 2018/00351; A61B 2018/00577;
(Continued)

(56) References Cited

U.S. PATENT DOCUMENTS 5,779,715 A   7/1998  Tu
6,419,674 B1  7/2002  Bowser et al.
(Continued)

FOREIGN PATENT DOCUMENTS

WO    2015168155 A1   11/2015

OTHER PUBLICATIONS

International Search Report and Written Opinion dated Jun. 8, 2017 for International Application No. PCT/US2017/025148.

*Primary Examiner* — Linda C Dvorak
*Assistant Examiner* — James A Cipriano
(74) *Attorney, Agent, or Firm* — Seager, Tufte & Wickhem LLP

(57) ABSTRACT

Extraction devices for extracting chronically implanted devices such as leadless cardiac pacemakers (LCP). In some cases, the extraction devices may be configured to cut, tear or ablate through at least some of the tissue ingrowth around and/or over the chronically implanted device such that a retrieval feature on the chronically implanted device may be grasped for removal of the chronically implanted device. Implantable medical devices such as LCPs may include features that facilitate their removal.

17 Claims, 31 Drawing Sheets

(51) Int. Cl.
*A61N 1/372* (2006.01)
*A61B 17/3205* (2006.01)
*A61B 17/3209* (2006.01)
*A61B 17/32* (2006.01)
*A61N 1/362* (2006.01)
*A61N 1/375* (2006.01)
*A61N 1/378* (2006.01)
*A61B 17/00* (2006.01)
*A61B 18/00* (2006.01)

(52) U.S. Cl.
CPC ........ *A61B 17/32056* (2013.01); *A61N 1/056* (2013.01); *A61N 1/0573* (2013.01); *A61N 1/362* (2013.01); *A61N 1/372* (2013.01); *A61N 1/3756* (2013.01); *A61N 1/3787* (2013.01); *A61N 1/37205* (2013.01); *A61B 18/1445* (2013.01); *A61B 2017/00358* (2013.01); *A61B 2017/320004* (2013.01); *A61B 2017/32006* (2013.01); *A61B 2018/00351* (2013.01); *A61B 2018/00577* (2013.01); *A61B 2018/00601* (2013.01); *A61B 2018/141* (2013.01); *A61N 2001/0578* (2013.01)

(58) Field of Classification Search
CPC .... A61B 2018/00601; A61B 2018/141; A61B 17/320016; A61B 17/32056; A61B 17/3209; A61B 2017/00358; A61B 2017/320004; A61B 2017/32006; A61N 1/056; A61N 1/0573; A61N 1/362–1/3624; A61N 1/372; A61N 1/37205; A61N 1/3756; A61N 1/3787; A61N 2001/0578

See application file for complete search history.

(56) References Cited

U.S. PATENT DOCUMENTS

| | | |
|---|---|---|
| 8,798,745 B2 | 8/2014 | Jacobson |
| 9,168,372 B2 | 10/2015 | Fain |
| 9,308,365 B2 | 4/2016 | Nordstrom et al. |
| 2002/0198581 A1* | 12/2002 | Sanchez-Zambrano ..................... A61N 1/0565 607/116 |
| 2005/0267555 A1 | 12/2005 | Marnfeldt et al. |
| 2012/0109148 A1 | 5/2012 | Bonner et al. |
| 2012/0165827 A1 | 6/2012 | Khairkhahan et al. |
| 2015/0142069 A1* | 5/2015 | Sambelashvili ..... A61N 1/3688 607/18 |
| 2015/0306381 A1 | 10/2015 | Schmidt et al. |
| 2018/0161039 A1* | 6/2018 | Harks ................ A61B 17/0057 |

* cited by examiner

CHRONICALLY IMPLANTABLE MEDICAL DEVICES CONFIGURED FOR EXTRACTION AND EXTRACTION DEVICES FOR EXTRACTING CHRONICALLY IMPLANTED MEDICAL DEVICES

CROSS REFERENCE TO RELATED APPLICATIONS

This application claims the benefit of U.S. Provisional Patent Application Ser. No. 62/397,915 filed on Sep. 21, 2016, and U.S. Provisional Patent Ser. No. 62/316,074 filed on Mar. 31, 2016, the disclosures of which are incorporated herein by reference.

TECHNICAL FIELD

The disclosure relates generally to extraction devices for extracting chronically implanted medical devices, as well as chronically implantable medical devices that are designed to facilitate removal.

BACKGROUND

Cardiac pacemakers such as leadless cardiac pacemakers are used to sense and pace hearts that are susceptible to a variety of incorrect heart rhythms, including but not limited to bradycardia, which is a slow heart rate, and tachycardia, which is a high heart rate. In some cases, there may be a desire to remove a previously implanted leadless cardiac pacemaker. Since these devices are designed for long life, in many cases substantial tissue growth (e.g. endothelialization) around and even over the leadless cardiac pacemaker may occur, particularly with chronically (long-term) implanted devices. Tissue growth can complicate removal of the implanted device. Accordingly, there is a desire to provide extraction devices that are directed at extracting chronically implanted devices such as but not limited to leadless cardiac pacemakers.

SUMMARY

The disclosure is directed to implantable medical devices that are configured to be more easily retrieved, even after chronic implantation. In some cases, an implantable medical device may include features that enable device retrieval. In some instances, for example, an implantable medical device may be configured to cut or ablate at least some of the tissue ingrowth around and/or over the implantable medical device such that a retrieval feature on the chronically implanted device may be grasped for removal of the chronically implanted device. In some cases, extraction devices may be configured to extract chronically implanted devices such as but not limited to leadless cardiac pacemakers (LCP). In some cases, these devices may be configured to cut or tear through at least some of the tissue ingrowth around and/or over the chronically implanted device such that a retrieval feature on the chronically implanted device may be grasped for removal of the chronically implanted device.

In an example of the disclosure, an implantable medical device (IMD) that is configured for deployment within a chamber of a patient's heart includes a housing that is configured to be positioned within the chamber of the patient's heart proximate a chamber wall. The housing extends from a distal end to a proximal end. A power source may be disposed within the housing. Circuitry may be disposed within the housing and may be operatively coupled to the power source. An electrode may be fixed relative to the housing and may be positioned to contact the chamber wall once the IMD is implanted. The circuitry may be configured to pace the patient's heart via the electrode. A fixation element for extending into the chamber wall at the implantation site to fix the IMD relative to the chamber wall at the implantation site may be disposed at or near the distal end of the housing. The IMD may include a retrieval feature for retrieving the IMD after implantation. The retrieval feature may be disposed at or near the proximal end of the housing. In some cases, the retrieval feature may be configured to expose at least part of the IMD to a surrounding blood pool, thus making the IMD accessible with other retrieval systems such as snares and catheters. In some cases, the retrieval feature may include an ablating region that is operatively coupled to the circuitry, wherein the circuitry is configured to selectively provide sufficient energy from the power source of the IMD to the ablating region to cause tissue proximate the retrieval feature to be ablated.

Alternatively or additionally to any of the embodiments above, the retrieval feature may include a tether ring that forms at least part of the ablating region.

Alternatively or additionally to any of the embodiments above, the IMD may further include a cutting feature disposed at or near the proximal end of the housing.

Alternatively or additionally to any of the embodiments above, the cutting feature may be actuatable from a retracted position in which the cutting feature is disposed within the housing to an extended position in which at least a portion of the cutting feature extends and faces proximally.

Alternatively or additionally to any of the embodiments above, the cutting feature may form at least part of the ablating region.

Alternatively or additionally to any of the embodiments above, the power source may have sufficient stored energy to provide sufficient energy to the ablating region of the retrieval feature to cause the ablating region to be heated sufficiently to ablate tissue proximate the retrieval feature.

Alternatively or additionally to any of the embodiments above, the IMD may further include an antenna operably coupled to the circuitry, the antenna configured to receive radiated energy directed towards the IMD from a location exterior to the patient and to provide the energy to the circuitry, and wherein the circuitry is configured to direct at least some of the energy to the power source and ultimately to the ablating region.

Alternatively or additionally to any of the embodiments above, the radiated energy includes ultrasound.

Alternatively or additionally to any of the embodiments above, the radiated energy includes RF energy.

Alternatively or additionally to any of the embodiments above, the IMD may be a leadless cardiac pacemaker (LCP).

In another example of the disclosure, an implantable medical device (IMD) configured for deployment within a patient may include a housing that is configured to be implantable within the patient at an implantation site as well as a fixation element for fixing the IMD to the patient at the implantation site. A retrieval feature may be secured relative to the housing for facilitating retrieval of the IMD from the implantation site. An extraction element may be secured relative to the housing, the extraction element may be configured to expose at least part of the retrieval feature from tissue overgrowth.

Alternatively or additionally to any of the embodiments above, the extraction element may be configured to expose at least part of the retrieval feature from tissue overgrowth by ablating at least some of the tissue overgrowth.

Alternatively or additionally to any of the embodiments above, the extraction element may be configured to expose at least part of the retrieval feature from tissue overgrowth by cutting at least some of the tissue overgrowth.

Alternatively or additionally to any of the embodiments above, the extraction element may include a heating element that is selectively operatively coupled to a power source to ablate tissue away from the retrieval feature.

Alternatively or additionally to any of the embodiments above, the heating element may include one or more heating elements that extend along an outer surface of the housing.

Alternatively or additionally to any of the embodiments above, the heating element may include one or more heating elements that extend along an outer surface of the housing in a spiral shape.

Alternatively or additionally to any of the embodiments above, the extraction element may include an energy-absorbable material that is sufficiently heated by an incident energy beam emanating from exterior to the patient to ablate or cut tissue overgrowth adjacent the extraction element.

In another example of the disclosure, an extraction device for removing a previously implanted Implantable Medical Device (IMD) includes a retrieval cavity at a distal region of the extraction device that is sized to fit over at least a proximal region of the IMB. The retrieval cavity may be configured to fit at least partially over tissue overgrowing the proximal region of the IMB. One or more electrodes may be disposed within the retrieval cavity and may be positioned adjacent the proximal region of the IMB when the proximal region of the IMD is positioned within the retrieval cavity. The one or more electrodes may be electrically coupled to one or conductors that can be connected to a source of ablating energy for ablating at least some of the tissue overgrowing the proximal region of the IMD.

Alternatively or additionally to any of the embodiments above, the extraction device may further include a retrieval loop that is extendable into the retrieval cavity and manipulatable from the proximal region of the extraction device by an operator. The retrieval loop may be configured to selectively engage a retrieval feature of the IMB once at least some of the tissue overgrowing the proximal region of the IMB has been ablated, and to pull the IMD into the retrieval cavity of the extraction device.

Alternatively or additionally to any of the embodiments above, the one or more electrodes extend partially around a circumference of the retrieval cavity such that the tissue overgrowing the IMB is only partially cut away by ablation, leaving a flap that prevents the cut tissue from migrating away.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE FIGURES

The disclosure may be more completely understood in consideration of the following detailed description in connection with the accompanying drawings, in which.

Figure 1:
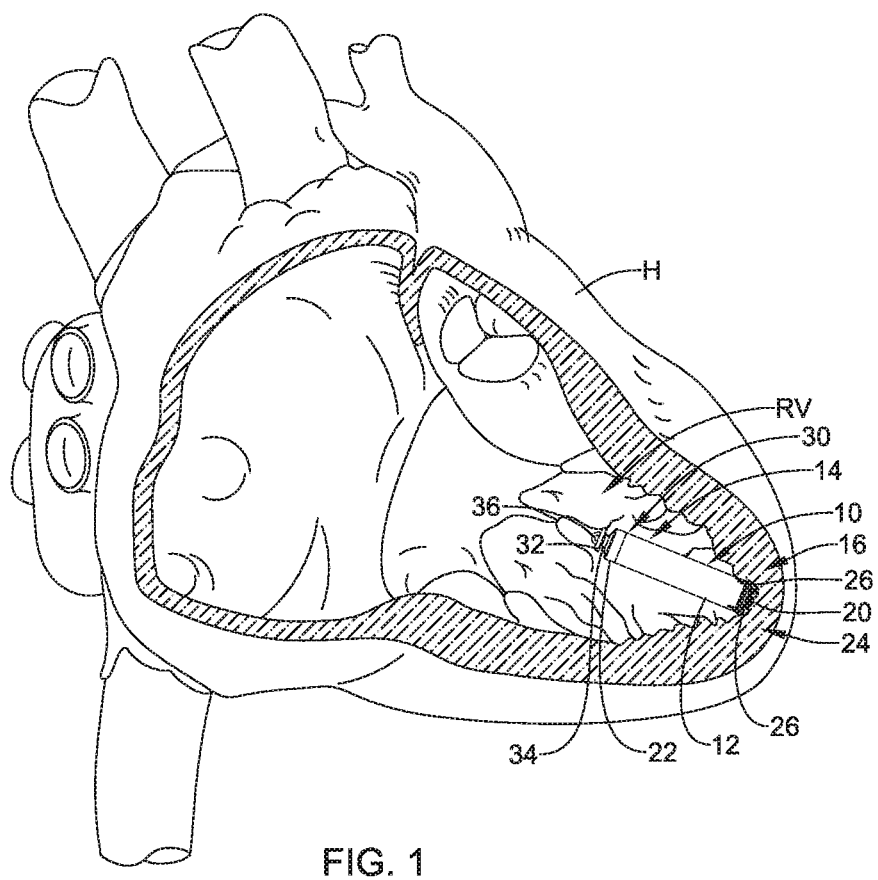
FIG. 1 is a partial cut away plan view of an example leadless pacing device implanted within a heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers may include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules that may, for example, be fixed to an intracardiac implant site in a cardiac chamber. In some cases, the small capsule may include bipolar pacing/sensing electrodes, a power source (e.g. a battery), and associated electrical circuitry for controlling the pacing/sensing electrodes, and thus may provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle.

While a leadless cardiac pacemaker is used as an example implantable medical device, the disclosure may be applied to any suitable implantable medical device including, for example, neuro-stimulators, diagnostic devices including those that do not deliver therapy, and/or any other suitable implantable medical device as desired.

Figure 2:
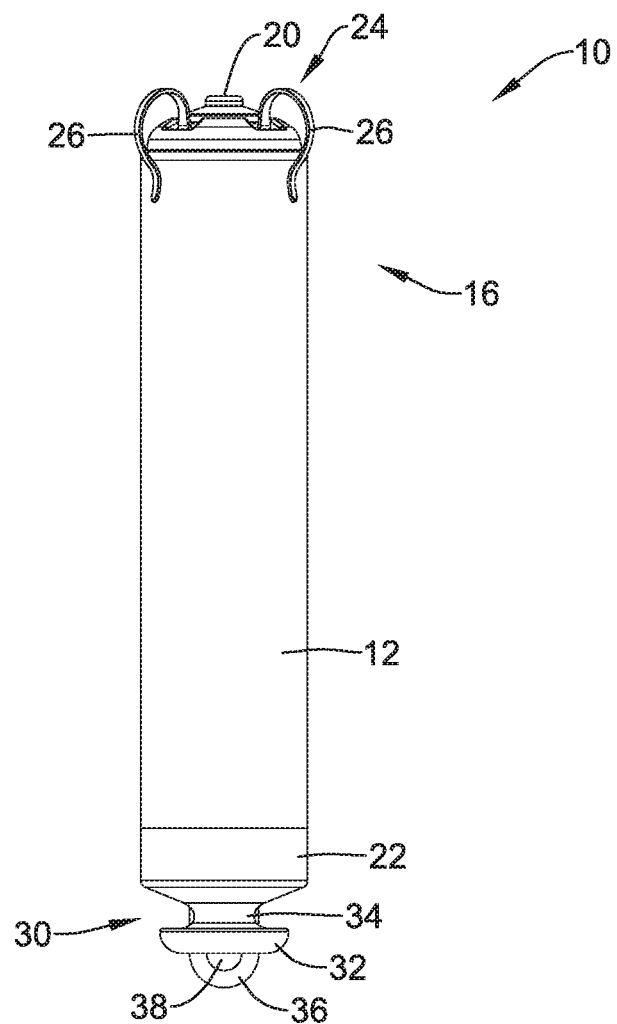
FIG. 2 is a side elevation view of an example implantable LCP device.

FIG. 1 illustrates an example implantable leadless cardiac pacing device 10 (e.g., a leadless pacemaker) implanted in a chamber of a heart H, such as the right ventricle RV. A side elevation view of the illustrative implantable medical device (IMD) 10 is shown in FIG. 2. The implantable device 10 may include a shell or housing 12 having a proximal end 14 and a distal end 16. In some instances, the IMD 10 may include a first electrode 20 positioned adjacent to the distal end 16 of the housing 12, and a second electrode 22 positioned adjacent to the proximal end 14 of the housing 12. In some cases, the housing 12 may include a conductive material and may be insulated at least a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be configured to be positioned against the cardiac tissue of the heart H or may otherwise contact the cardiac tissue of the heart H while the second electrode 22 may be spaced away from the first electrode 20, and thus spaced away from the cardiac tissue.

The illustrative IMD 10 may include a pulse generator (e.g., electrical circuitry) and a power source (e.g., a battery) within the housing 12 to provide electrical signals to the electrodes 20, 22 and thus control the pacing/sensing electrodes 20, 22. In some cases, electrical communication between the pulse generator and the electrodes 20, 22 may provide electrical stimulation to heart tissue and/or sense a physiological condition.

The IMD 10 may include a fixation mechanism 24 proximate the distal end 16 of the housing 12 configured to attach the IMD 10 to a tissue wall of the heart H, or otherwise anchor the IMD 10 to the anatomy of the patient. As shown in FIG. 1, in some instances, the fixation mechanism 24 may include one or more, or a plurality of hooks or tines 26 anchored into the cardiac tissue of the heart H to attach the IMD 10 to a tissue wall. In other cases, the fixation mechanism 24 may include one or more, or a plurality of passive tines, configured to entangle with trabeculae within the chamber of the heart H and/or a helical fixation anchor configured to be screwed into a tissue wall to anchor the IMD 10 to the heart H. These are just some examples.

The IMD 10 may include a docking member 30 proximate the proximal end 14 of the housing 12 configured to facilitate delivery and/or retrieval of the IMD 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the IMD 10 which is greater than a radial dimension of the neck portion 34 from the longitudinal axis of the IMD 10. In some cases, the docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The docking member 30 may be configured to facilitate delivery of the IMD 10 to the intracardiac site and/or retrieval of the IMD 10 from the intracardiac site. FIG. 2 shows one example docking member configuration. However, it is contemplated that any suitable docking member configuration may be used, as desired.

In some cases, the docking member 30, or at least a portion thereof, may be considered as providing a retrieval feature generally shown at 40 that may subsequently be grasped in order to retrieve the IMD 10 subsequent to implantation. The retrieval feature 40 may be grasped, for example, by a variety of different devices, such as but not limited to a retrieval loop, forceps and the like. In some cases, retrieval of a chronically implanted IMD 10, meaning that the IMD 10 has been in place within the anatomy for a period of time ranging from several months to multiple years, may be complicated by tissue ingrowth around part or even all of the IMD 10, including the retrieval feature 40. In some cases, it may be useful to cut through or otherwise remove at least some of the tissue ingrowth prior to actually retrieving the IMD 10.

Figure 3:
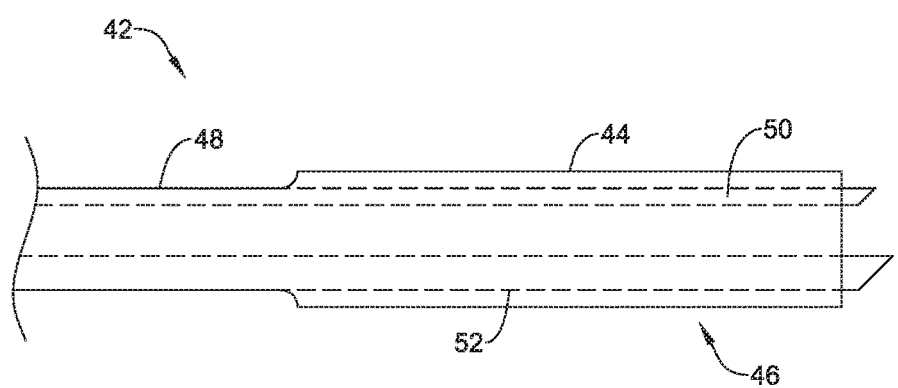
FIG. 3 is a schematic view of an illustrative extraction device according to an example of the disclosure.

FIG. 3 provides a highly schematic view of a distal portion of an illustrative extraction device 42. The illustrative extraction device 42 includes a retrieval cavity 44 disposed at a distal region 46 of the extraction device 42. The more proximal portions of the extraction device 42 are not shown, including a proximal portion that may be manipulated by an operator of the extraction device. In some cases, the retrieval cavity 44 is sized and otherwise configured to accommodate at least part of the IMD 10 therein once the IMD 10 has been extracted from the heart tissue and has been withdrawn into the retrieval cavity 44. In some cases, the retrieval cavity 44 has a length sufficient to accommodate the entire IMD 10, and the retrieval cavity 44 has an inner diameter that is sufficient to accommodate the IMD 10. In some cases, the retrieval cavity 44 has an inner diameter that is sufficient to simultaneously accommodate the IMD 10 as well as one or more additional tools or other devices extending through the extraction device 42 and into the retrieval cavity 44. In some cases, the retrieval cavity 44 extends distally from an extraction device shaft 48.

In some cases, as noted, other tools and other devices may be used in combination with the extraction device 42, and/or may be included as part of the extraction device 42. As seen in FIG. 3, a relatively smaller diameter tool 50 and a relatively larger diameter tool 52, seen in phantom, may be disposed within and extend distally from the retrieval cavity 44. In some cases, the relatively smaller diameter tool 50 may represent a retrieval loop, or a needle, or perhaps a wire that can be bent into a shape to cut into ingrowth tissue. In some cases, the relatively larger diameter tool 52 may represent a pair of grasping forceps, or perhaps a funnel that can be extended to help cut through ingrowth tissue. Illustrative but non-limiting examples of these tools 50, 52 will be discussed with respect to subsequent Figures. In each of the subsequent Figures, the IMD 10 is shown as being an LCP 54 including a retrieval feature 56, and is covered or at least substantially covered by ingrowth tissue 58.

Figure 4:
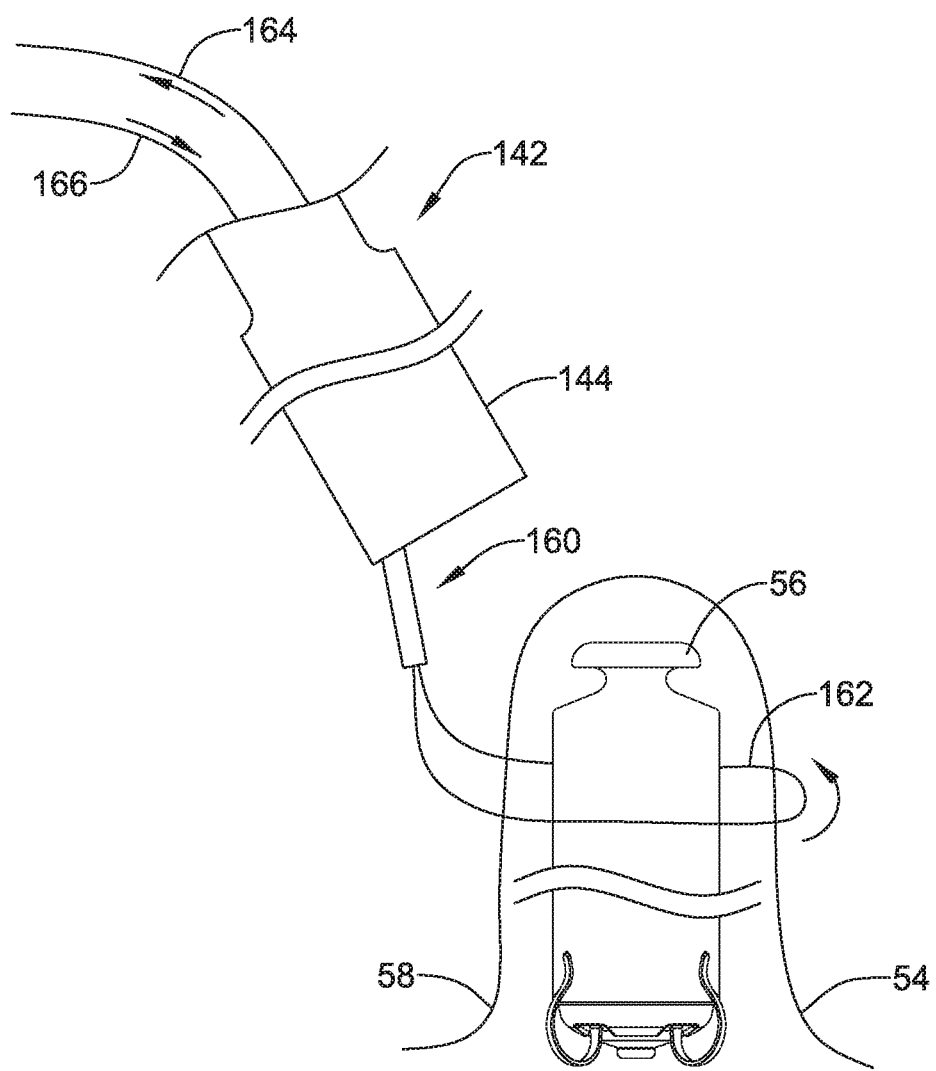
FIG. 4 is a schematic view of an illustrative extraction device extracting a chronically implanted LCP according to an example of the disclosure.

FIG. 4 is a schematic diagram of an illustrative extraction device 142, which may be considered as being an example of the extraction device 42 (FIG. 3). A distal portion of the illustrative extraction device 142 includes a retrieval cavity 144. The more proximal portions of the extraction device 142 are not shown, including a proximal portion that may be manipulated by an operator of the extraction device. The retrieval loop 160 may include a loop 162 and first and second control wires 164, 166. The loop 162 may extend distally from the retrieval cavity 144. In some cases, the retrieval loop 160 may be considered as being an example of the relatively smaller diameter tool 50 (FIG. 3), but this is not required. In some cases, the first and second control wires 164, 166 may be electrically active, and a portion of the loop 162 may be electrically exposed in order to conduct RF energy for the purposes of cutting through at least some of the ingrowth tissue 58. In some cases, a cutaneous patch (not shown) may be used as a return electrode.

It will be appreciated that by moving the first and second control wires 164, 166 together, the loop 162 may be advanced distally from the retrieval cavity 144 or withdrawn proximally towards and into the retrieval cavity 144. Appropriate manipulation of the first and second control wires 164, 166 may also be used to make the loop 162 smaller or larger, as desired. Manipulation of the first and second control wires 164, 166 in opposite directions may be used to slide a portion of the loop 162 back and forth relative to the ingrowth tissue 58 in a cutting motion. After cutting away sufficient ingrowth tissue 58 using the retrieval loop 160 to expose and then grasp the retrieval feature 40, the retrieval loop 160 may be withdrawn proximally to pull the LCP 54 into the retrieval cavity 144.

Figure 5:
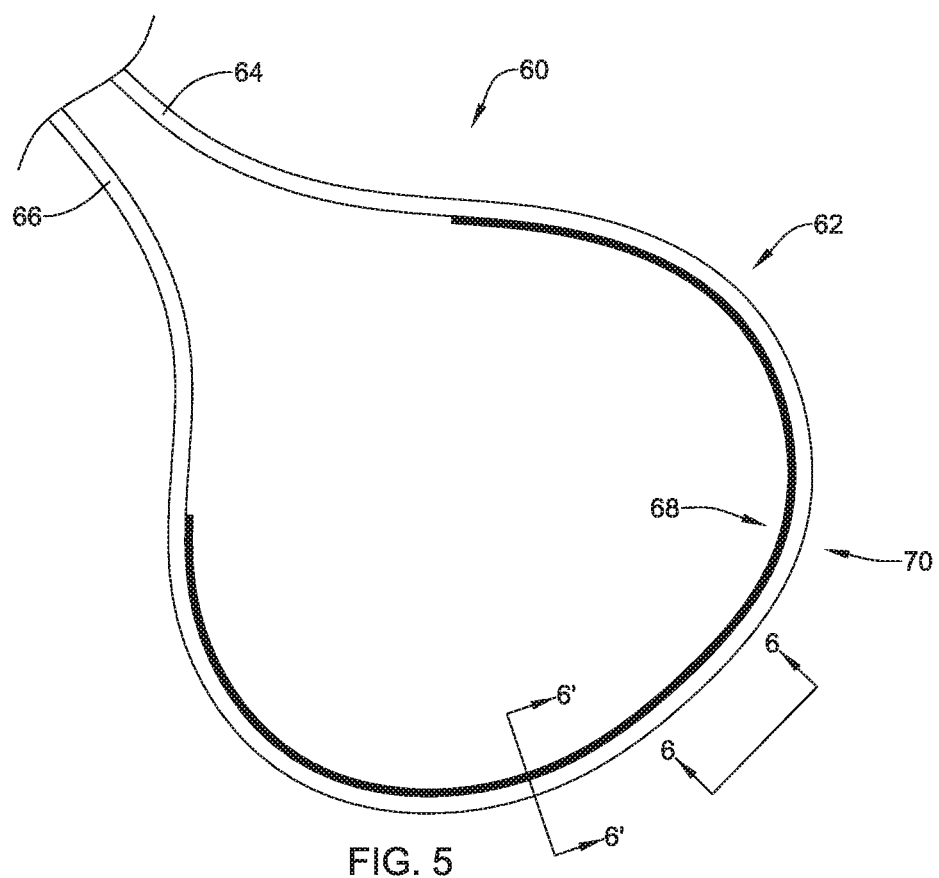
FIG. 5 is an enlarged view of an illustrative retrieval loop forming part of the extraction device of FIG. 4.

In some cases, the loop 162 may be configured to cut or tear through the ingrowth tissue 58 as the loop 162 moves relative to the ingrowth tissue 58. FIG. 5 is an enlarged view of an illustrative retrieval loop 160. As can be seen in FIG. 5, in some cases the retrieval loop forms a loop 162 that has an inside surface 168 and an outer surface 170. In some cases, the inside surface 168, or a first surface, may be configured to cut, abrade or otherwise disrupt the ingrowth tissue 58. In some cases, the outer surface 170, or a second surface, may not be configured to cut, abrade or otherwise disrupt the ingrowth tissue 58. In some cases, the outside surface may be smooth. As a result, the inside surface 168 may be used to cut through the ingrowth tissue 58 while the outer surface 170 may be configured to not damage other nearby tissue (e.g. the heart wall). In some cases, the loop 162 may be used to cut around the LCP 54, exposing the retrieval feature 40. With reference to FIG. 4, once the retrieval feature 40 is exposed, the loop 162 may be tightened around the retrieval feature 40 of the LCP 54, and then may be used to pull the LCP 54 into the retrieval cavity 144. Once the LCP is in the retrieval cavity 144, the extraction device and the LCP 54 may be removed from the body.

Figure 6A:
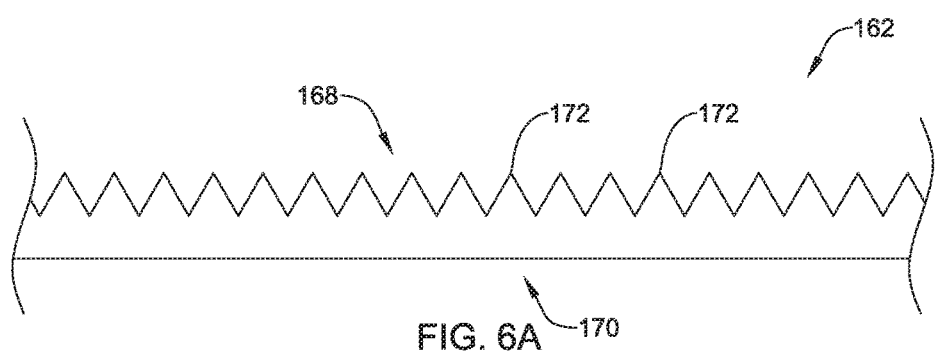
FIGS. 6A and 6B are enlarged schematic views of two example cutting surfaces of the illustrative retrieval loop of FIG. 5, taken along line 6-6 of FIG. 5.
Figure 6B:
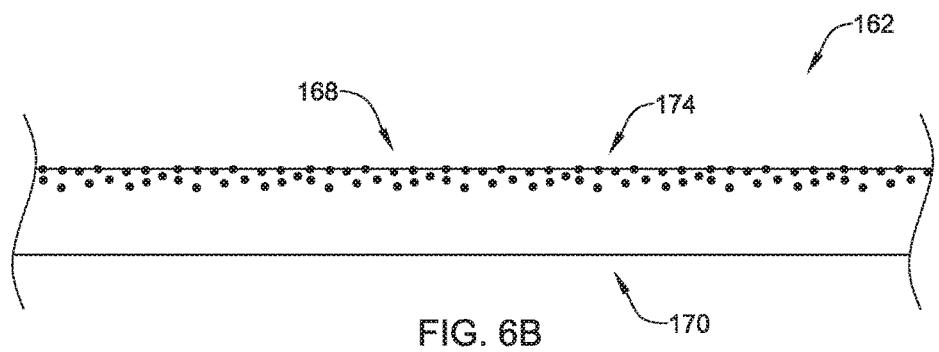
Figure 6C:
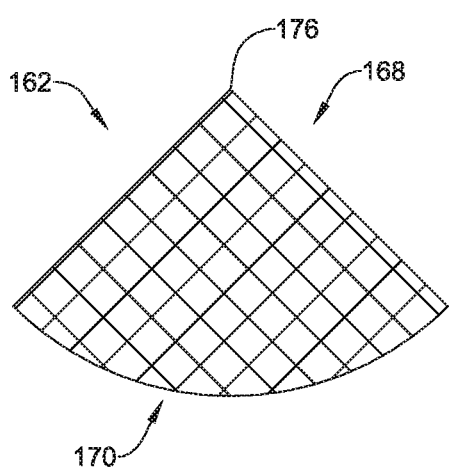
FIG. 6C is a schematic cross-sectional view showing an illustrative cutting surface of the illustrative retrieval loop of FIG. 5, taken along line 6'-6' of FIG. 5.

FIGS. 6A and 6B are enlarged schematic views of two example cutting surfaces of the illustrative retrieval loop of FIG. 5, taken along line 6-6 of FIG. 5. In both FIG. 6A and FIG. 6B, the loop 162 includes an inside surface 168 and an outer surface 170. In FIG. 6A, the inside surface 168 includes a plurality of teeth 172. It will be appreciated that as the loop 162 is slide back and forth relative to the ingrowth tissue 58, the teeth 172 will cut through the ingrowth tissue 58. In this example, the outer surface 170 is relatively smooth. In FIG. 6B, the inside surface 168 includes an abrasive surface 174. In some cases, the abrasive surface 174 may include an abrasive material that is deposited onto the inside surface 168. In some cases, the abrasive surface 174 may instead be the result of etching the inside surface 168 to form a roughened and abrasive surface. In the example shown, the outer surface 170 does not include the abrasive surface 174, and instead is relatively smooth to limit peripheral tissue damage during use of the retrieval loop 162. FIG. 6C is a cross-sectional view through the loop 162, and shows another example in which the inside surface 68 has a blade-like cutting surface 176 which may, for example, may cut more smoothly through the ingrowth tissue 58, and in some cases may tear less.

Figure 7:
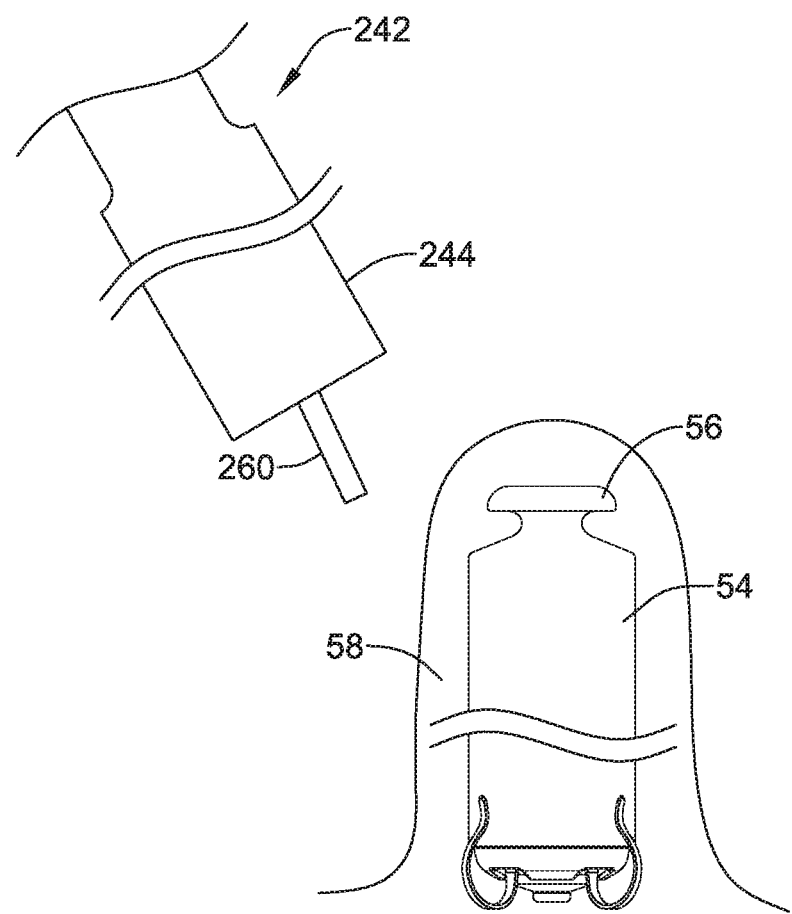
FIG. 7 is a schematic view of an illustrative extraction device extracting a chronically implanted LCP according to an example of the disclosure.

FIG. 7 is a schematic illustration of another illustrative extraction device 242, which may be considered as being an example of the extraction device 42 (FIG. 3). A distal portion of the illustrative extraction device 242 includes a retrieval cavity 244. The more proximal portions of the extraction device 242 are not shown, including a proximal portion that may be manipulated by an operator of the extraction device. In this example, a hollow needle 260 may be extended from the retrieval cavity 244 and may for example be considered as an example of the relatively larger tool 52 (FIG. 3). In some cases, the hollow needle 260 may be in fluid communication with a source (not shown) of saline, or perhaps contrast solution such that the hollow needle 260 may be able to penetrate through the ingrowth tissue 58 and reach a location proximate the LCP 54. Injecting fluid through the hollow needle 260 may, for example, help to loosen some of the ingrowth tissue 58 away from the outer surface of the LCP 54. Penetrating the ingrowth tissue 58 may also help reduce a vacuum that might otherwise develop when attempting to withdraw the LCP 54 from the ingrowth tissue 58.

Figure 8:
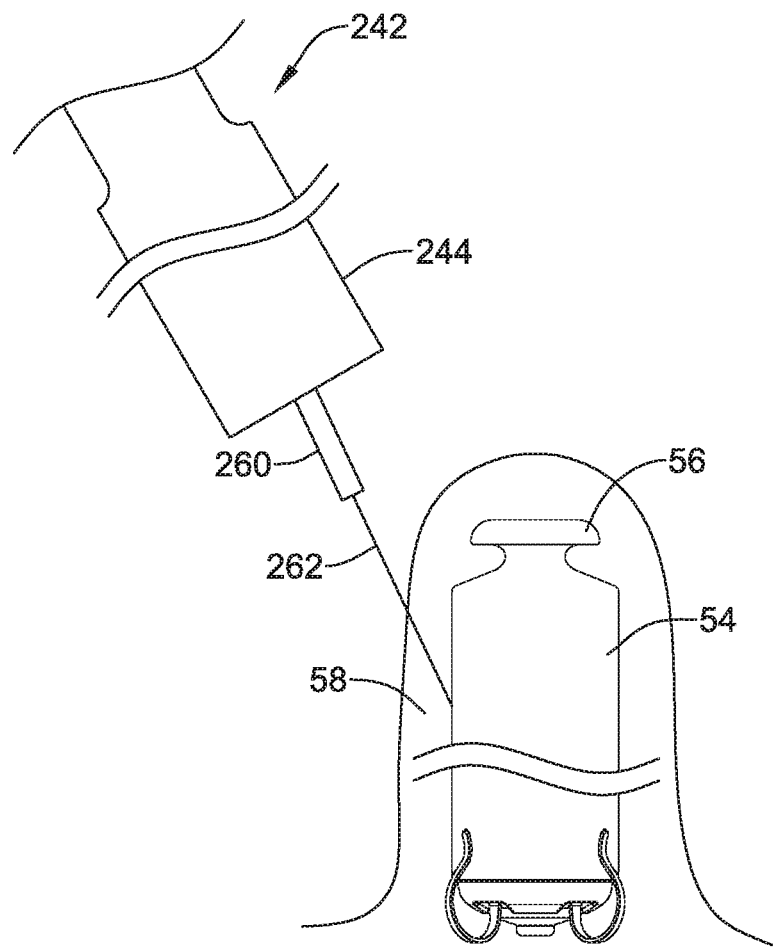
FIG. 8 is a schematic view of an illustrative extraction device extracting a chronically implanted LCP according to an example of the disclosure.

In some cases, as shown in FIG. 8, an elongated probe 262 may be advanced through the hollow needle 260 (or advanced adjacent the hollow needle 260) and may be moved about the LCP 54 in a radial direction indicated by an arrow 264 to score and break away some of the ingrowth tissue 58. The elongated probe 262 may have a pre-bent shape that it assumes once advanced out of the hollow needle 260 and may have a cutting edge. The pre-bent shape may be configured to bend around and track the outer surface of the housing of the LCP 54, as shown. In some cases, the elongated probe 262 may be considered a pre-shaped cutting stylet.

The elongated probe 262 may be moved longitudinally along the length of the housing of the LCP to separate the ingrowth tissue 58 from the housing of the LCP 54, and to cut the ingrowth tissue to expose the retrieval feature 56 of the LCP 54. In some cases, the hollow needle 260 (and elongated probe 262) may then be withdrawn and a retrieval loop such as the retrieval loop 60 (FIG. 4) may be advanced to engage the retrieval feature 56 and withdraw the LCP 54 into the retrieval cavity 244.

Figure 9:
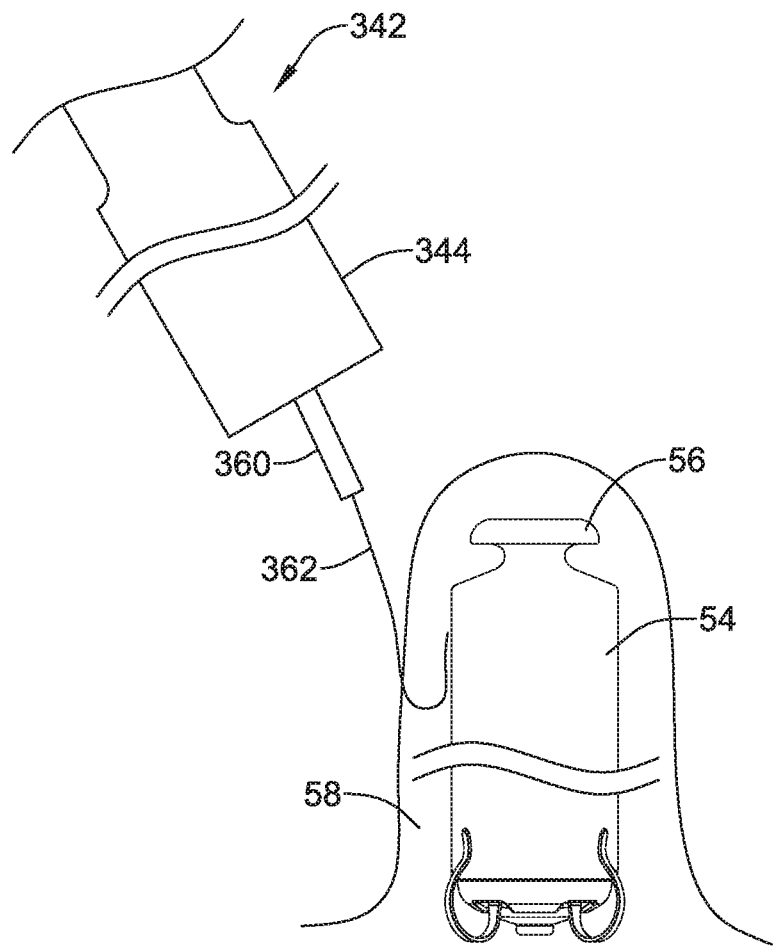
FIG. 9 is a schematic view of an illustrative extraction device extracting a chronically implanted LCP according to an example of the disclosure.

FIG. 9 is a schematic illustration of another illustrative extraction device 342, which may be considered as being an example of the extraction device 42 (FIG. 3). A distal portion of the illustrative extraction device 342 includes a retrieval cavity 344. The more proximal portions of the extraction device 342 are not shown, including a proximal portion that may be manipulated by an operator of the extraction device. In the example shown, a deflectable probe 360 may be advanced distally from the retrieval cavity 344 and may be used to penetrate into the ingrowth tissue 58. In some cases, the deflectable probe 360 may be considered as extending from an elongated tube 362, which in some cases may be considered as being an example of the relatively larger diameter tool 52 (FIG. 3). Penetrating the ingrowth tissue 58 may also help reduce a vacuum that might otherwise develop when attempting to withdraw the LCP 54 from the ingrowth tissue 58. The deflectable probe 360 may, in some cases, be deflected into a hook-shape once advanced out of the elongated tube 362. The hook can be withdrawn proximally to tear or otherwise remove some of the ingrowth tissue 58 to expose the retrieval feature 56 of the LCP 54. In some cases, the deflectable probe 360 may then be withdrawn and a retrieval loop such as the retrieval loop 60 (FIG. 4) may be advanced to engage the retrieval feature 56 and withdraw the LCP 54 into the retrieval cavity 344.

Figure 10:
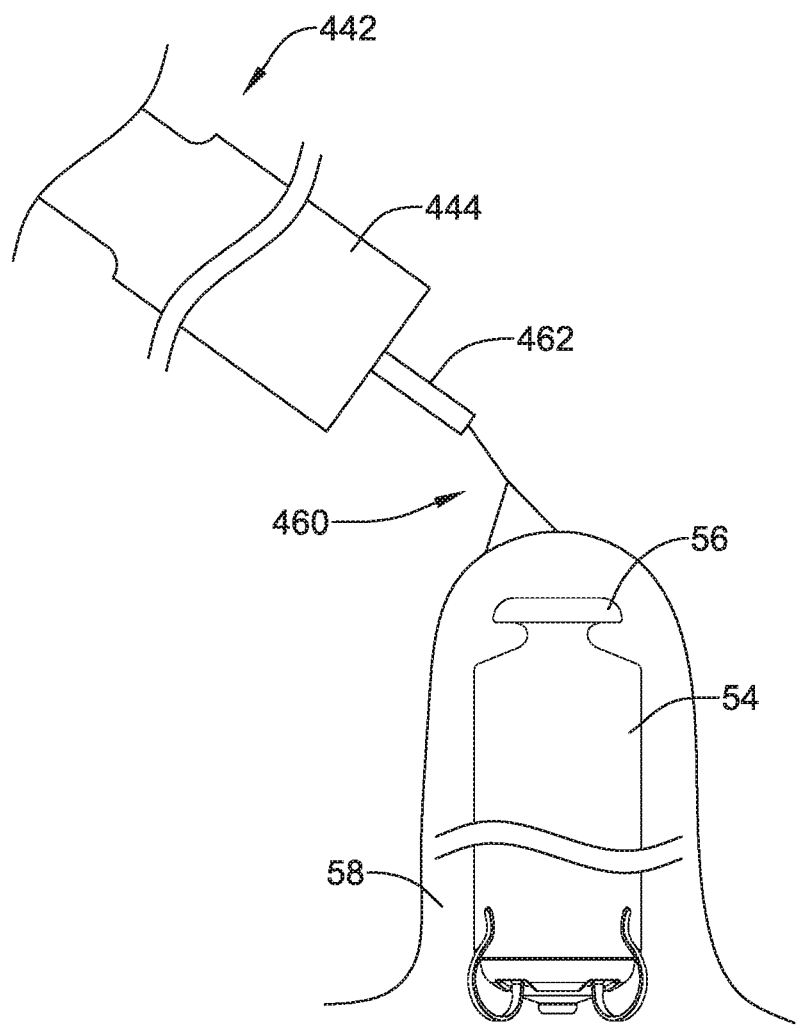
FIG. 10 is a schematic view of an illustrative extraction device extracting a chronically implanted LCP according to an example of the disclosure.

FIG. 10 is a schematic diagram of another illustrative extraction device 442, which may be considered as being an example of the extraction device 42 (FIG. 3). A distal portion of the illustrative extraction device 442 includes a retrieval cavity 444. The more proximal portions of the extraction device 442 are not shown, including a proximal portion that may be manipulated by an operator of the extraction device. In some cases, a grasping forceps 460 may be distally extendable from an elongate tube 462 that may, for example, be considered as being an example of the relatively larger diameter tool 52 (FIG. 3). The grasping forceps 460 may be used to grasp and tear away at the ingrowth tissue 58. In some cases, the grasping forceps 460 may be electrically active and may be used to transmit RF energy to cut the ingrowth tissue. Once the retrieval feature 56 is exposed, the grasping forceps 460 may be used to engage the retrieval feature 56 and withdraw the LCP 54 into the retrieval cavity 444. In other cases, the grasping forceps 460 may be withdrawn, and a retrieval loop such as the retrieval loop 60 (FIG. 4) may be advanced to engage the retrieval feature 56 and withdraw the LCP 54 into the retrieval cavity 444.

Figure 11:
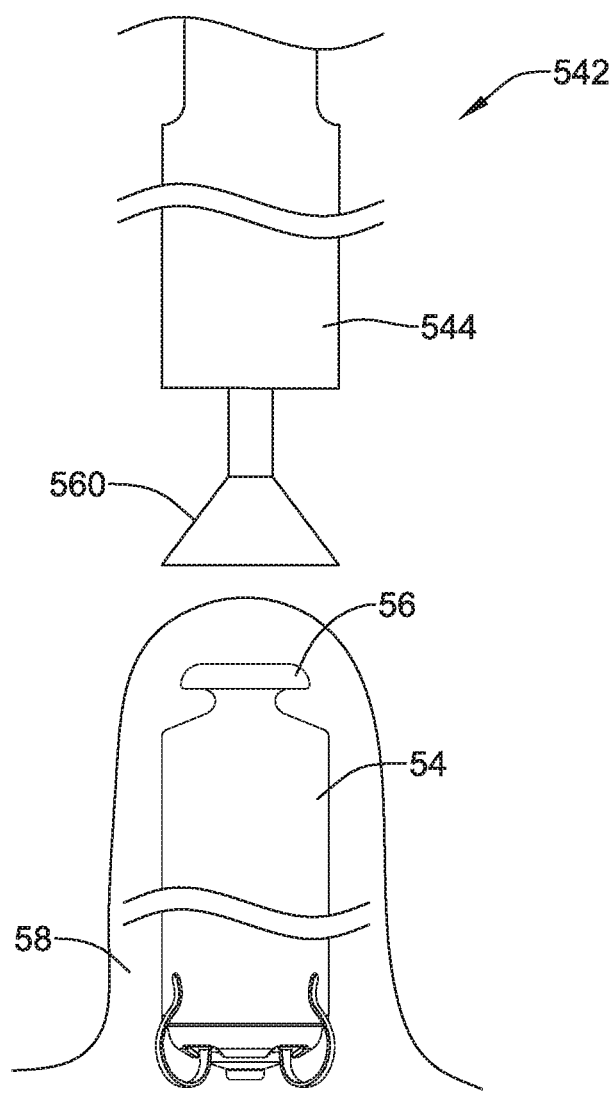
FIG. 11 is a schematic view of an illustrative extraction device extracting a chronically implanted LCP according to an example of the disclosure.
Figure 12:
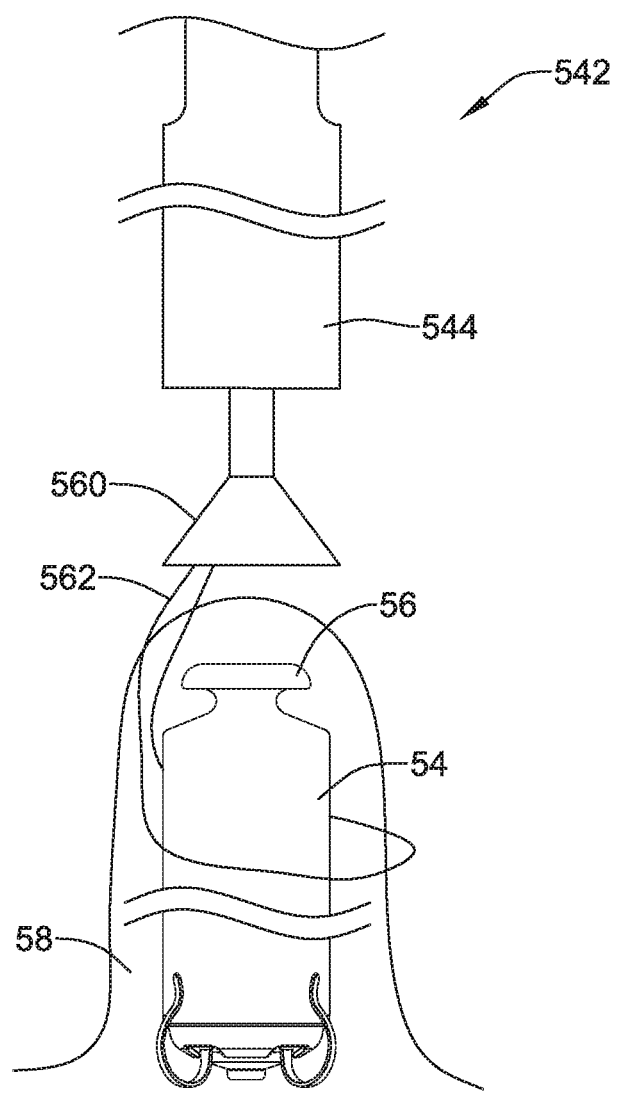
FIG. 12 is a schematic view of an illustrative extraction device extracting a chronically implanted LCP according to an example of the disclosure.
Figure 14:
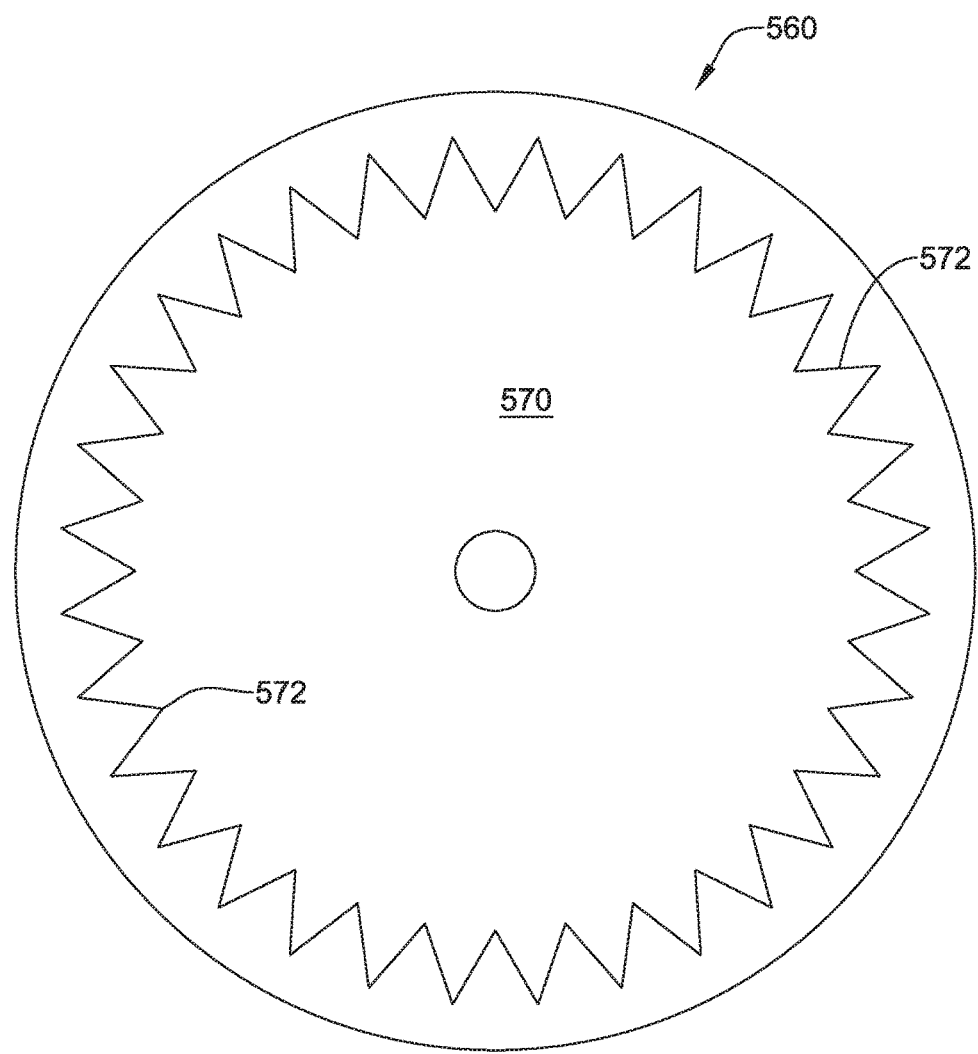
FIG. 14 is an enlarged view of a mouth of the funnel used in the extraction devices shown in FIGS. 11 through 13.

FIG. 11 is a schematic diagram of an illustrative extraction device 542, which may be considered as being an example of the extraction device 42 (FIG. 3). A distal portion of the illustrative extraction device 542 includes a retrieval cavity 544. The more proximal portions of the extraction device 242 are not shown, including a proximal portion that may be manipulated by an operator of the extraction device. In this example, an extendable funnel 560 is extendable from the retrieval cavity 544. In some cases, as shown for example in FIG. 14, the extendable funnel 560 may include a plurality of teeth 572 disposed on an inner surface 570 of the extendable funnel 560. As a result, and returning to FIG. 11, the extendable funnel 560 may be advanced into contact with the ingrowth tissue 58 and then rotated to cut through the ingrowth tissue 58. In some cases, the extendable funnel 560 may be considered as being an example of the relatively larger diameter tool 52 (FIG. 3). Once the retrieval feature 56 is exposed, and as shown in FIG. 12, a retrieval loop 562 (much like the retrieval loop 60 of FIG. 4) may be advanced, sometimes through the extendable funnel 560 or adjacent the extendable funnel 560, to engage the retrieval feature 56 and withdraw the LCP 54 into the retrieval cavity 344.

Figure 13:
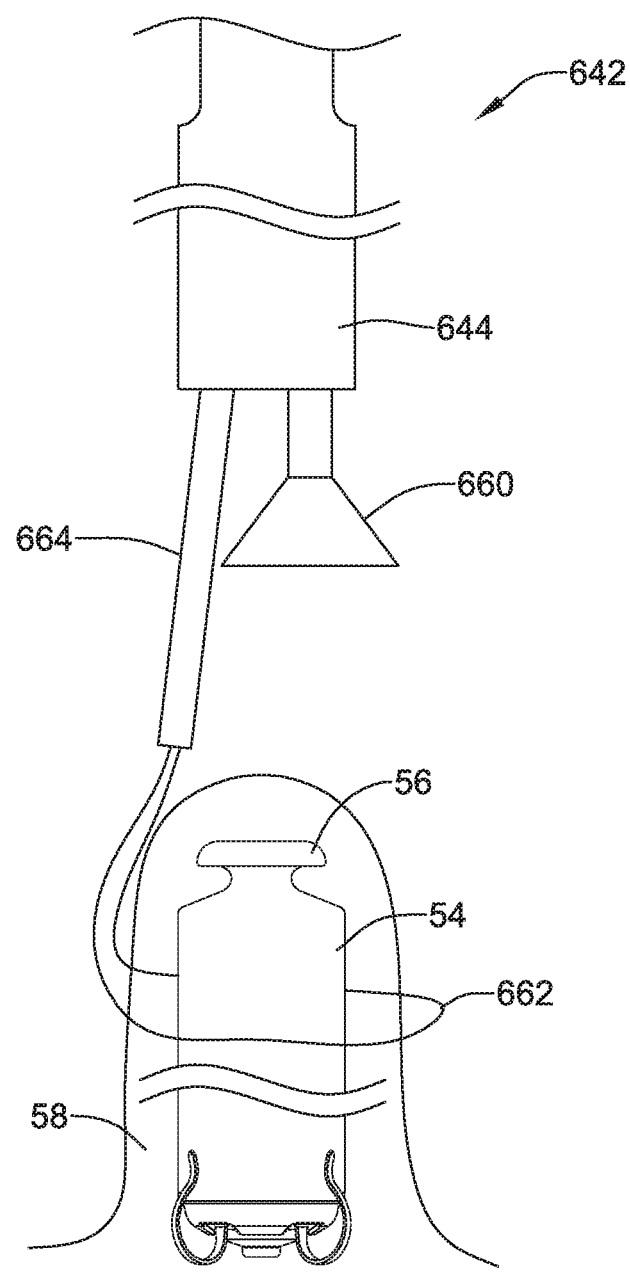
FIG. 13 is a schematic view of an illustrative extraction device extracting a chronically implanted LCP according to an example of the disclosure.

FIG. 13 is a schematic diagram of an illustrative extraction device 642, which may be considered as being an example of the extraction device 42 (FIG. 3). A distal portion of the illustrative extraction device 642 includes a retrieval cavity 644. The more proximal portions of the extraction device 642 are not shown, including a proximal portion that may be manipulated by an operator of the extraction device. The extraction device 642 is similar to the extraction device 542, including an extendable funnel 660, and a retrieval loop 662, but also includes a retrieval loop sheath 664. In some cases, the retrieval loop sheath 664 may be located off-center within the retrieval cavity 644. In some cases, this permits other tools to be inserted distally through the retrieval cavity 644 in a more centered orientation. In some cases, the extendable funnel 660 includes internally located teeth, much like the teeth 572 shown in FIG. 14.

Figure 15:
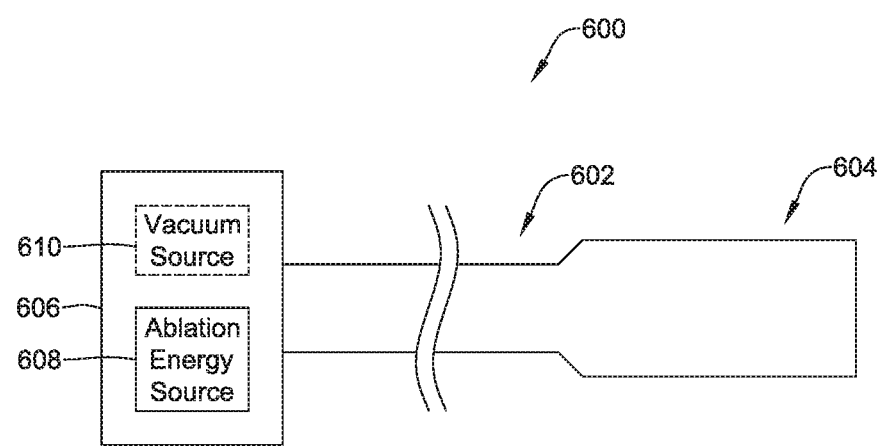
FIG. 15 is a schematic view of an illustrative extraction system according to an example of the disclosure.

FIG. 15 is a schematic view of an illustrative extraction system 600. The extraction system 600 includes an elongated catheter 602 extending distally to a retrieval cavity 604. It will be appreciated that the retrieval cavity 604 may be sized to have internal dimensions that permit an implanted IMD to fit at least partially into the retrieval cavity 604, even if there is tissue growth over part or all of the implanted IMD. In the example shown, the elongated catheter 602 extends proximally to an apparatus 606. In some cases, as illustrated, the apparatus 606 includes an ablation energy source 608 that may be configured to provide ablation energy from the apparatus 606 to features located within the retrieval cavity 604, as will be discussed in more detail with respect to FIG. 16. Optionally, the apparatus 606 may include a vacuum source 610 that may be operably coupled to the elongated catheter 602 and hence the retrieval cavity 604 such that vacuum may be applied to extract debris that could become dislodged in the extraction process.

Figure 16:
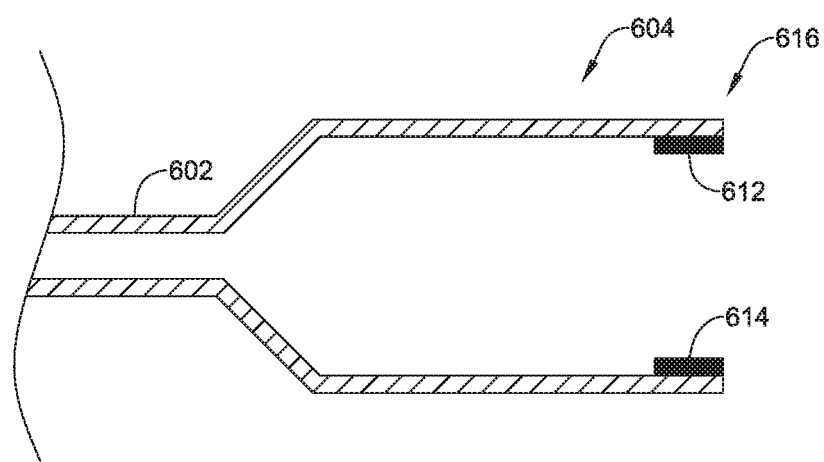
FIG. 16 is a schematic cross-sectional view of an extraction device forming a portion of the illustrative extraction system of FIG. 15.

The retrieval cavity 604 is better illustrated in FIG. 16. In the example shown, a pair of electrodes 612 and 614 are disposed at or near a distal end 616 of the retrieval cavity 604. In some cases, the electrodes 612, 614 may also function as radiopaque marker bands to facilitate guidance of the retrieval cavity 604 under fluoroscopy, for example. While not expressly illustrated, it will be appreciated that the electrodes 612, 614 may be electrically connected to the ablation energy source 608 (FIG. 15) via electrical conductors such as wiring traces extending proximally from the electrodes 612, 614 and along the body of the elongated catheter 602. In some cases, the electrodes 612, 614 are disposed within the retrieval cavity 604 at locations that enable the electrodes 612, 614 to be near or come into contact with tissue growth covering at least part of an IMD that is to be extracted. Ablation energy may be applied via the electrodes 612, 614 to the tissue. The ablation energy may be sufficient to ablate at least some of the overgrowing tissue and thus make extraction of the IMD easier.

Figure 17:
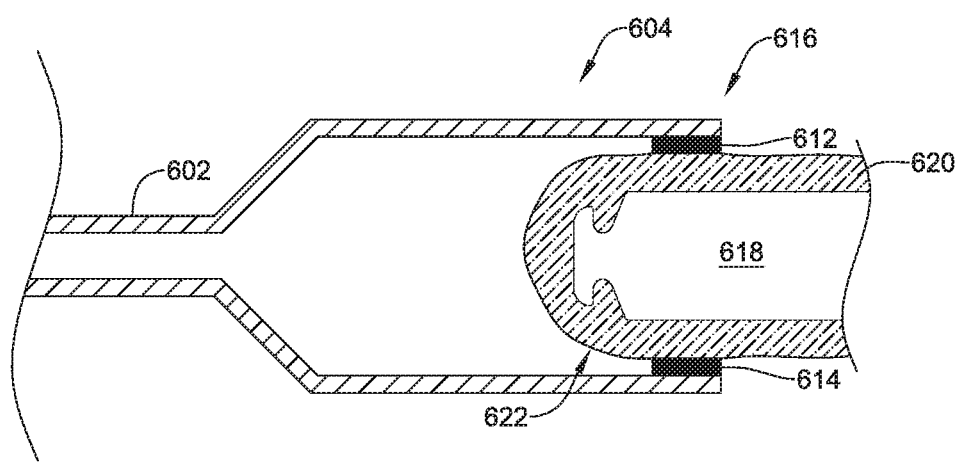
FIGS. 17 through 19 illustrate, in sequence, an example of extracting an implanted medical device using the illustrative extraction system of FIG. 15.
Figure 18:
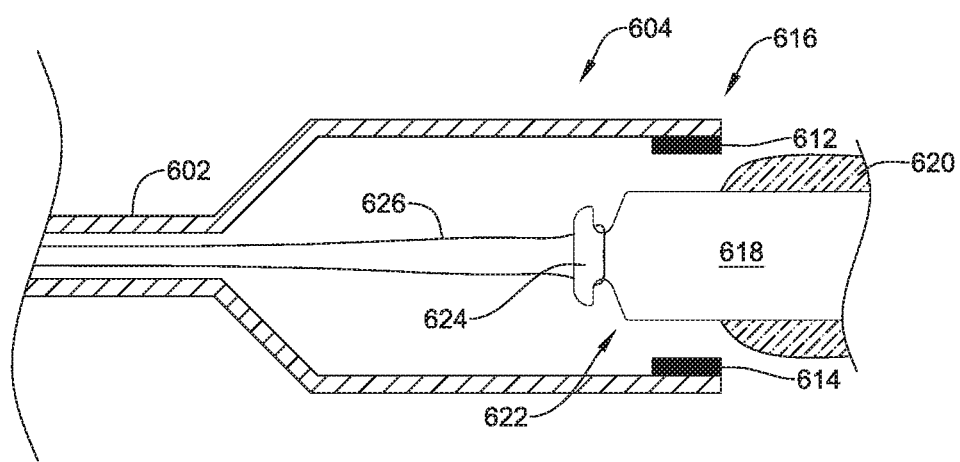
Figure 19:
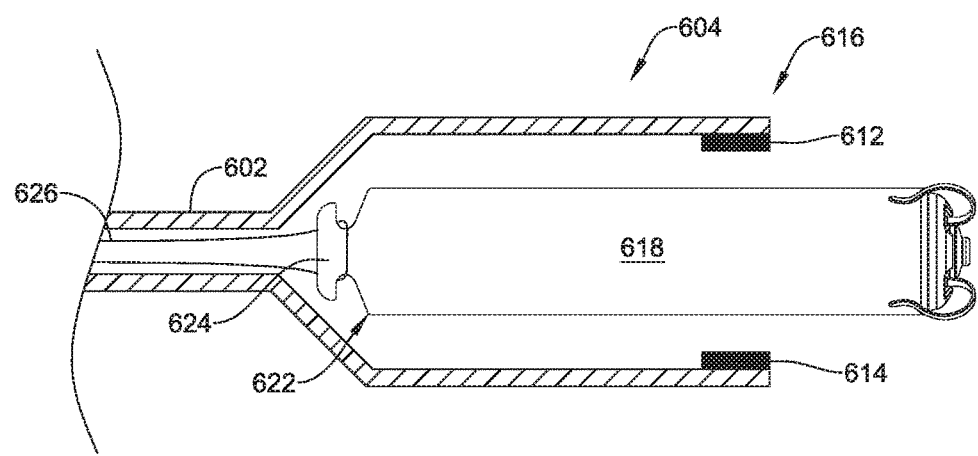

FIGS. 17 through 19 provide an illustrative but non-limiting example of how the extraction system 600 may be used to remove a chronically implanted IMD 618 that is at least partially overgrown with tissue growth 620. As can be seen in FIG. 17, the retrieval cavity 604 is able to extend distally over at least a proximal portion 622 of the IMD 618. In some cases, for example, the retrieval cavity 604 may be extended distally over at least the proximal portion 622 of the IMD 618 until the electrodes 612, 614 are near or come into contact with the tissue growth 620. Ablation energy may be applied to the tissue growth 620 via the electrodes 612, 614, causing at least some of the tissue growth 620 to be ablated.

In FIG. 18, it can be seen that at least some of the tissue growth 620 has been ablated away, exposing the proximal portion 622 of the IMD 618. In some cases, the proximal portion 622 of the IMD 618 may include a retrieval feature 624 that may be grasped via a snare 626 or the like that has been extended distally through the elongated catheter 602 and into the retrieval cavity 604. While the retrieval feature 624 is illustrated as having a knob shape, it will be appreciated that a variety of different retrieval features are contemplated. The snare 626 may be manipulated from a proximal end of the elongated catheter 602, for example. Once the snare 626 has been secured about the retrieval feature 624, the snare 626 may be pulled proximally to urge the IMD 618 proximally into the retrieval cavity 604. This is shown for example in FIG. 19. The elongated catheter 602, along with the snared IMD 618, may then be withdrawn from the patient's body.

Figure 20:
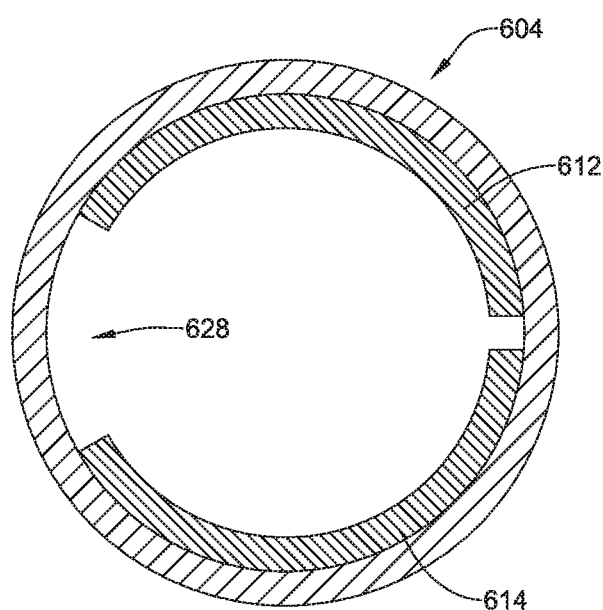
FIG. 20 is a schematic end view of the extraction device forming a portion of the illustrative extraction system of FIG. 15.

FIG. 20 shows an illustrative but non-limiting plan view of the distal end of the retrieval cavity 604, looking proximally. In some cases, the electrodes 612, 614 may be configured to ablate in a continuous or near-continuous circle about the IMD 618. In some cases, radio frequency ablation is used. In such cases, a suitable radio frequency signal is applied to the electrodes 612, 614 to generate sufficient heat energy to ablate the tissue growth 620 near the electrodes. In some instances, vacuum may be applied during the ablation process in order to retrieve any debris that might be dislodged during the ablation process. In some cases, the electrodes 612, 614 may be configured to ablate only partially around a circumference of the IMD 618. As shown in FIG. 20, the electrodes 612 and 614 may be spaced by a sufficient gap 628 along part of the circumference of the IMD such that the tissue growth 620 in this region is not ablated. This may result in a flap of tissue growth 620 that is sufficient to hold the tissue growth 620 to prevent the tissue growth from floating away while still permitting access to the retrieval feature 624.

In some cases, cryoablation may be used. When so provided, one or more bladders may be positioned along the inside of the retrieval cavity 604. The one more bladders may be fed by one or more passageways extending along the elongated catheter 602. A suitable gas such as liquid nitrogen or argon gas may be pumped through the passageways and into the one or more bladders to create intense cold to freeze and destroy (cryoablate) the tissue growth 620.

FIGS. 1 through 20 provide examples of extraction devices that may be used to extract a chronically implanted medical device that may or may not include and particular features incorporated into the chronically implanted medical device that may facilitate removal of the chronically implanted medical device. FIGS. 21 through 28 and 30 provide illustrative but non-limiting examples of implantable medical devices that include features to help facilitate their subsequent removal. It will be appreciated that particular features shown on one of these implantable medical devices may be combined with features shown on one or more other of the implantable medical devices. In some cases, some of these implantable medical devices may, for example, be leadless cardiac pacemakers (LCPs), implantable monitors (IM), and/or any other implantable medical device (IMD) as desired.

Figure 21:
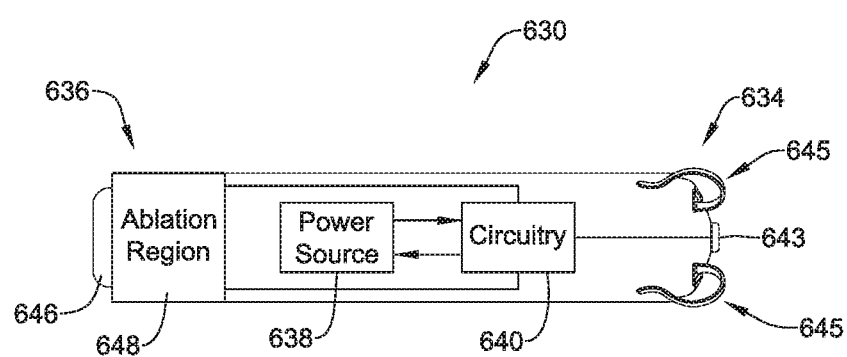
FIG. 21 is a schematic diagram of an illustrative implantable medical device (IMD) that includes features to facilitate subsequent retrieval of the IMD after implantation according to an example of the disclosure.

FIG. 21 provides a schematic view of an implantable medical device (IMD) 630 that is configured for deployment within a chamber of a patient's heart. The IMD 630 includes a housing 632 that may be configured to be positioned within the chamber of the patient's heart proximate a chamber wall. The housing extending from a distal end 634 to a proximal end 636. A power source 638 may be disposed within the housing. The power source 638 may be a non-rechargeable battery or a rechargeable battery, for example. Circuitry 640 may be disposed within the housing and may be operatively coupled to the power source 638. If the power source 638 is a rechargeable battery, the circuitry 640 may be configured to oversee and control the recharging process. An electrode 643 may be fixed relative to the housing 632 and may be positioned to contact the chamber wall once the IMD 630 is implanted. The circuitry 640 may be configured to pace the patient's heart via the electrode 643. The IMD 630 may include one or more fixation elements 645 for extending into the chamber wall at the implantation site to fix the IMD 630 relative to the chamber wall at the implantation site. The fixation element 645 may be disposed at or near the distal end 634 of the housing 632. As illustrated, a pair of fixation elements 645 in the form of fixation tines are shown. The illustrative IMD 630 may further include a retrieval feature 646 for subsequent retrieval of the IMD 630 after implantation. In some cases, the retrieval feature 646, which is shown schematically, may be disposed at or near the proximal end 636 of the housing 632. The retrieval feature 646 may take any desired form, such as but not limited to a knob form or a loop that can be grasped, for example.

In some cases, the retrieval feature 646 may include an ablating region 648 that is operably coupled to the circuitry 640. In some cases, the circuitry 640 may be configured to selectively provide sufficient energy from the power source 638 to the ablating region 648 to cause tissue proximate the retrieval feature 646 to ablate. In some cases, the ablating region 648 may include two or more electrodes, and the circuitry 640 may apply a suitable radio frequency signal to the two or more electrodes to generate sufficient heat energy to ablate the tissue growth near the electrodes.

Figure 22:
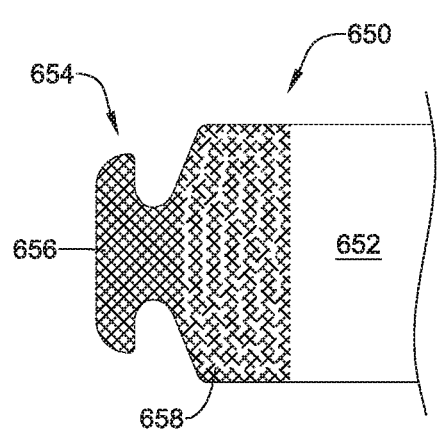
FIG. 22 is a schematic view of a proximal portion of an illustrative IMD that is representative of the IMD of FIG. 21.

FIG. 22 is a schematic illustration of a portion of an implantable medical device (IMD) 650 having a housing 652 and a retrieval knob 654 extending proximally from the housing 652. As illustrated, the retrieval knob 654 may form at least a portion of the ablating region, as indicated by the cross-hatching 656. In some cases, the ablating region may extend distally over a portion of the housing 652, as indicated by the phantom cross-hatching 658. The ablating region may be configured to receive ablating energy and thus ablate at least some of the tissue growth covering part or all of the retrieval knob 654 of the IMD 650.

Figure 23:
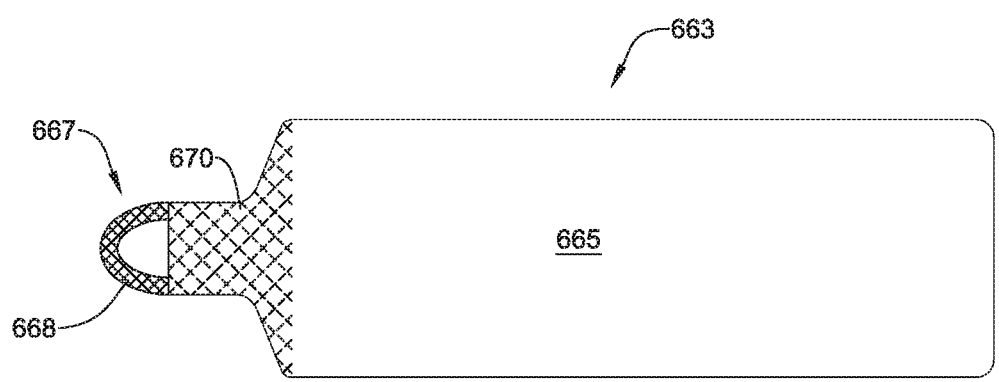
FIG. 23 is a schematic view of a proximal portion of an illustrative IMD that is representative of the IMD of FIG. 21.

FIG. 23 is a schematic illustration of an implantable medical device (IMD) 660 having a housing 665 and a tether ring 667 that extends proximally from the housing 665. In some cases, the tether ring 667 may accommodate a tether (not illustrated) that is useful during initial deployment of the IMD 663. The tether ring 667 may also be graspable for extraction. As illustrated, the tether ring 667 forms at least a portion of the ablating region, as indicated by the cross-hatching 668. In some cases, the ablating region extends distally over a portion of the housing 665, as indicated by the phantom cross-hatching 670. The ablating region may be configured to receive ablating energy and thus ablate at least some of the tissue growth covering part or all of the tether ring 667 of the IMD 663.

Figure 24:
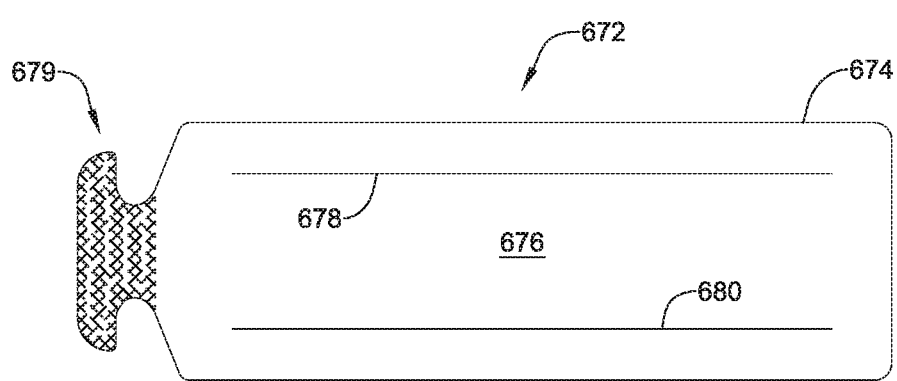
FIG. 24 is a schematic view of an illustrative IMD that is representative of the IMD of FIG. 21.

FIG. 24 is a schematic illustration of an implantable medical device (IMD) 672 having a housing 674. In some cases, as illustrated, the housing 674 may define an outer surface 676. In some cases, the outer surface 676 may include a first ablating region 678 and a second ablating region 680. While two distinct regions are shown, it will be appreciated that this is merely illustrative and the outer surface 676 may include any number of ablating regions. Each ablating region may include two or more electrodes. In other cases, each ablating region 678 and 680 may be a single electrode, and a separate common or ground electrode may be provided. In some cases, the common or ground electrode may service two or more of the ablating regions 678 and 680. Any other suitable arrangement may also be used.

In some cases, applying ablating energy to the first ablating region 678 and/or the second ablating region 680 (and any other ablating regions that may be present) may facilitate extraction by ablating tissue growth and/or interfering with the suction that may otherwise occur when trying to pull the IMD 672 out of the tissue growth at least partially encapsulating the IMD 672.

In some cases, the first ablating region 678 and/or the second ablation region 680 (and any other ablation regions) may be resistively heated by passing a current through the first ablating region 678 and/or the second ablation region 680, from one end to the other. In some cases, such as for RF ablation, a separate common or ground electrode 679 may be provided, so that a suitable radio frequency signal may be applied between the first ablating region 678 and/or the second ablating region 680 and the common or ground electrode 679 to generate sufficient heat to ablate the tissue growth along filament. These are just a few example implementations.

Figure 25:
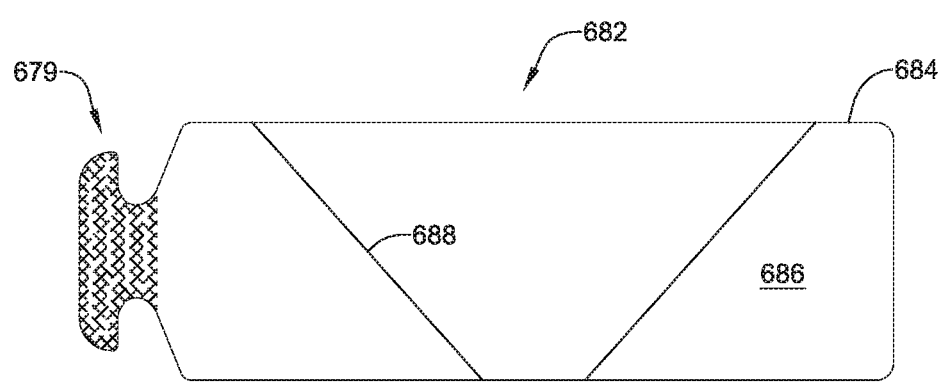
FIG. 25 is a schematic view of an illustrative IMD that is representative of the IMD of FIG. 21.

FIG. 25 is a schematic illustration of an implantable medical device (IMD) 682 having a housing 684. In some cases, as illustrated, the housing 684 may define an outer surface 686. In some cases, the outer surface 686 may include an ablating region 688 that extends around the housing 684 in a spiral or barber pole fashion. In some cases, the ablating region 688 may be a single ablating region. In some instances, the ablating region 688 may include two or more distinct ablating regions. Each ablating region 688 may include two or more electrodes. In some cases, the two or more electrodes may be interdigitated. In some cases, applying ablating energy to the ablating region 688 may facilitate extraction by ablating tissue growth and/or by interfering with the suction that may otherwise occur when trying to pull the IMD 682 out of the tissue growth at least partially encapsulating the IMD 682. In some cases, the ablating region 688 may be resistively heated by passing a current through the ablating region 688, from one end to the other. In some cases, such as for RF ablation, a separate common or ground electrode 679 may be provided, so that a suitable radio frequency signal may be applied between the ablating region 688 and the common or ground electrode 679 to generate sufficient heat to ablate the tissue growth along filament. These are just a few example implementations.

Figure 26:
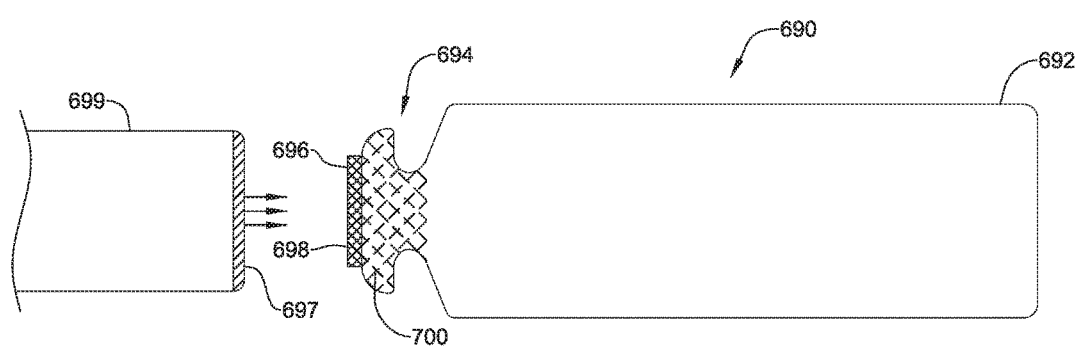
FIG. 26 is a schematic view of an illustrative IMD that is representative of the IMD of FIG. 21.

In some cases, ablation may not be the only way that an implantable medical device (IMD) may assist in its own extraction. In some cases, the IMD may be configured to cut through at least some of the tissue growth that partially or completely covers the IMD. FIG. 26, for example, is a schematic illustration of an implantable medical device (IMD) 690 having a housing 692. A retrieval feature 694 extends proximally from the housing 692. In some cases, as illustrated, a cutting feature 696 may extend proximally from the retrieval feature 694. In some cases, the cutting feature 696 may be fixed in place. In some cases, the cutting feature 696 and/or the retrieval feature 694 may form at least a portion of an ablating region, as indicated by the phantom cross-hatching 698 shown on the cutting feature 696 and the phantom cross-hatching 700 shown on the retrieval feature 694, but this is not required. In some cases, the cutting feature 696 may be aided in cutting through tissue growth by virtue of the tissue growth being pressed between the cutting feature 696 and a distal end 697 of a catheter 699 that may be extended distally towards the cutting feature 696.

Figure 27:
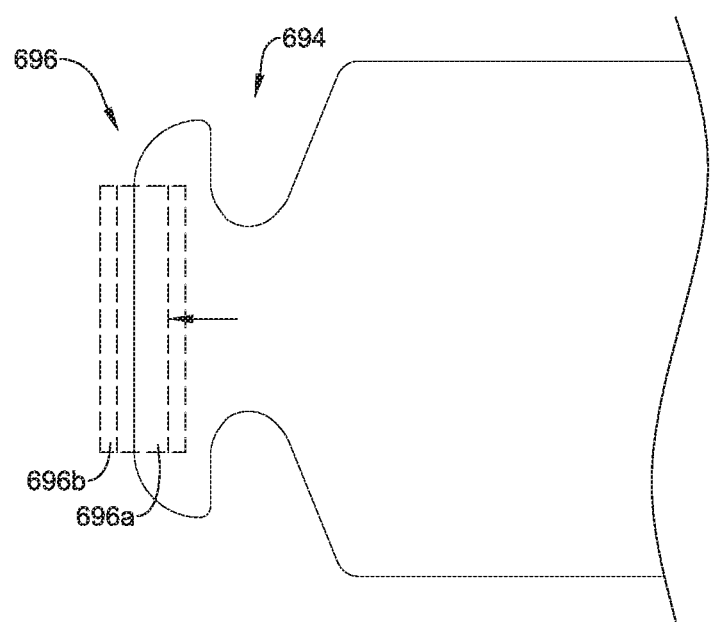
FIG. 27 is a schematic close up view of a portion of the illustrative IMD of FIG. 26.

In some cases, the cutting feature 696 may not be fixed in place, but may instead be movable. FIG. 27 is a schematic illustration of the retrieval feature 694 of FIG. 26. As can be seen, the cutting feature 696 may be actuatable from a retracted position indicated as 696a in which the cutting feature 696 is disposed at least partially within the retrieval feature 694 or otherwise within the housing 692 and an extended position indicated as 696b in which the cutting feature 696 extends proximally. In some cases, the distal end 697 of the catheter 699 (FIG. 26) may be used to help facilitate cutting.

Figure 28:
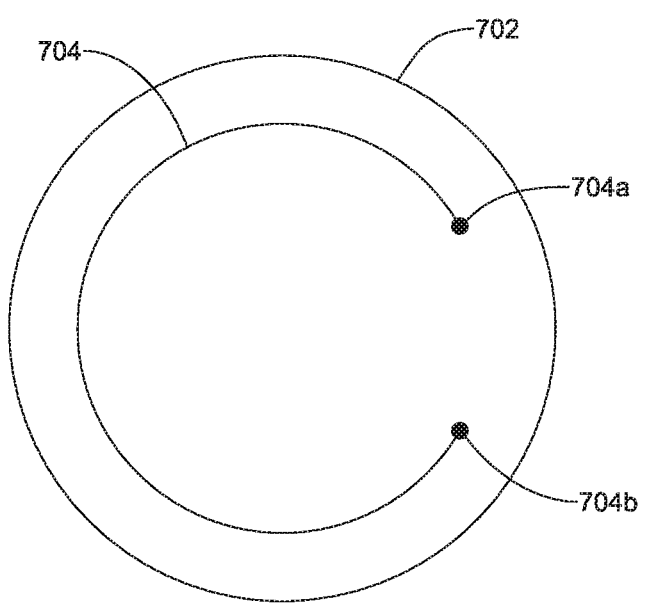
FIG. 28 is a schematic proximal end view of an illustrative IMD that is representative of the IMD of FIG. 21.

FIG. 28 shows an illustrative but non-limiting view of a proximal end of an implantable medical device (IMD) 702. In some cases, the IMD 702 may include a filament 704 that extends partially around the circumference of the proximal end, from a starting point 704a to an ending point 704b. The filament 704 may be operably coupled to the circuitry 640 and power source 638 (FIG. 21) such that ablating energy may be applied to the filament 704 in order to ablate at least some of the tissue growth covering part or all of the IMD 702. As can be seen, in some cases the filament 704 does not complete a continuous circle on the proximal end, but rather there is a gap between the starting point 704a and the ending point 704b. As a result, a flap may be formed in the tissue growth that keeps the tissue growth from floating away while still permitting access to the IMD 702.

In some cases, a separate common or ground electrode may be provided, so that a suitable radio frequency signal may be applied between filament 704 and the common or ground electrode to generate sufficient heat to ablate the tissue growth along filament. In other cases, the filament 704 may be a resistive heating element, and the circuit 640 may be configured to supply current through the filament to generate sufficient heat to ablate the tissue growth along filament. These are just a few example implementations.

Figure 29:
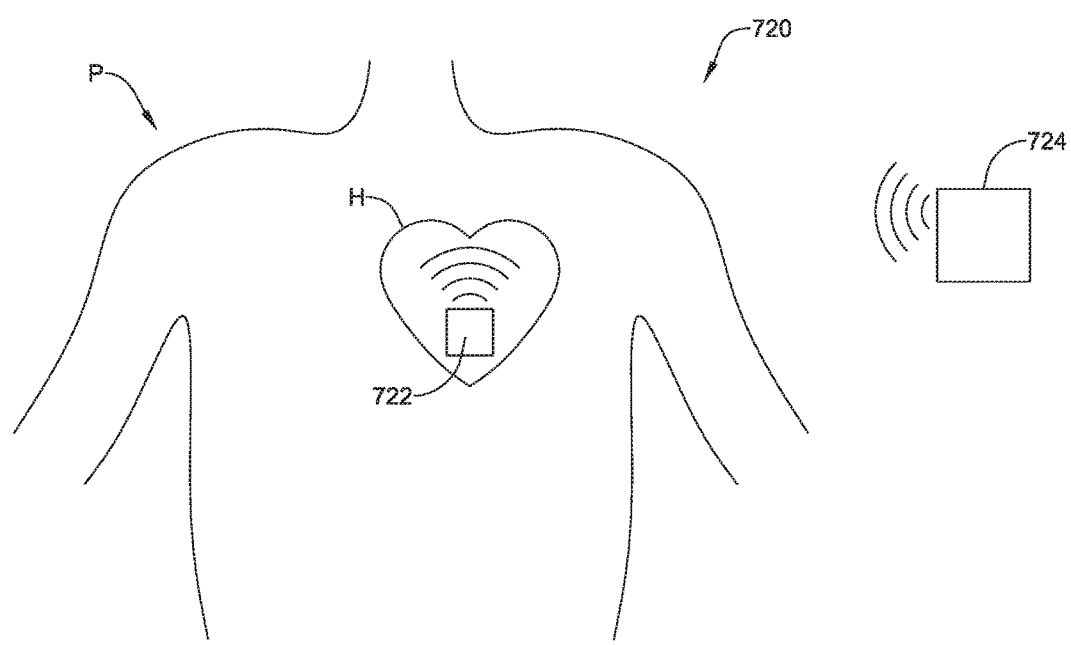
FIG. 29 is a schematic view of an illustrative system in which energy is fed into an implanted IMD from a position outside of the patient.

In some cases, the power source 638 (FIG. 21) may have sufficient stored energy to provide sufficient energy to the ablating region of the retrieval feature to cause the ablating region to be heated sufficiently to ablate tissue proximate the retrieval feature, whether it is the ablating region 648 (FIG. 21) or the particular examples of ablating regions shown in FIGS. 22-25 and 28. In some cases, the power source 638 may not have enough energy remaining to provide sufficient energy for ablation. FIG. 29 schematically shows a system 720 in which a patient P has an implantable medical device (IMD) 722 implanted within their heart H as well as an external device 724 that may be configured to transmit energy to the IMD 722. In some cases, the external device 724 transmits energy that is directly captured by one or more ablation regions disposed on or about the IMD 722 that, in response, heat adjacent tissue growth sufficiently to ablate the tissue. In some cases, the energy transmitted by the external device 724 is instead captured by the IMD 722 and used to recharge the power source 638 and/or provide additional ablating energy.

Figure 30:
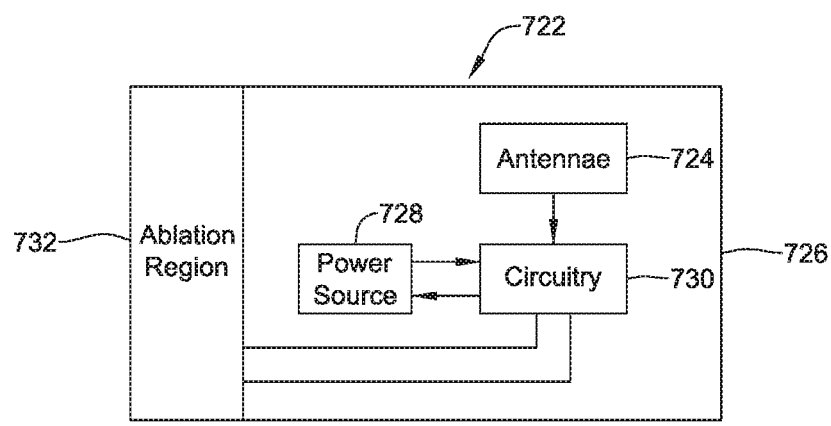
FIG. 30 is a schematic view of an IMD that may be used in the system of FIG. 29.

FIG. 30 is a schematic illustration of the IMD 722, configured to capture energy transmitted from the external device 724 and to use the captured energy to recharge or augment the power source 728. The IMD 722 includes a housing 726 that may be configured to be positioned within the chamber of the patient's heart proximate the chamber wall. The power source 728 may be disposed within the housing 726. The power source 728 may be a non-rechargeable battery or a rechargeable battery, for example. Circuitry 730 may be disposed within the housing 726 and may be operatively coupled to the power source 728. If the power source 728 is a rechargeable battery, the circuitry 730 may be configured to oversee and control the recharging process. The IMD 722 may include an ablating region 732 that is operably coupled to the circuitry 730. In some cases, the circuitry 730 may be configured to selectively provide sufficient energy from the power source 728 to the ablating region 732 to cause tissue proximate the ablating region 732 to ablate. The illustrative IMD 722 includes an antenna 734 that is operably coupled to the circuitry 730. The antenna may be configured to receive radiated energy directed towards the IMD 722 from a location exterior to the patient P, such as from the external device 724 (FIG. 29) and to provide the energy to the circuitry 730. The antenna may be configured to receive radio frequency (RF) energy. In some cases, the antenna may include a coil that is configured to inductively receive energy. The circuitry 730 is configured to direct at least some of the energy to the power source 728 and ultimately to the ablating region 732.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device (IMD) configured for deployment within a chamber of a patient's heart, the chamber including a chamber wall, the IMD comprising:
   a housing configured to be positioned within the chamber of the patient's heart proximate the chamber wall once the IMD is implanted, the housing extending from a distal end to a proximal end;
   a power source disposed within the housing;
   circuitry disposed within the housing and operatively coupled to the power source;
   an electrode fixed relative to the housing and positioned to contact the chamber wall once the IMD is implanted, the circuitry configured to pace the patient's heart via the electrode;
   a fixation element for extending into the chamber wall at the implantation site to fix the IMD relative to the chamber wall at the implantation site, the fixation element disposed at or near the distal end of the housing;
   a retrieval feature for retrieving the IMD after implantation, the retrieval feature disposed at or near the proximal end of the housing; and
   the retrieval feature including an ablating region that is operatively coupled to the circuitry, wherein the circuitry is configured to selectively provide sufficient energy from the power source to the ablating region to cause tissue proximate the retrieval feature to ablate and to expose the IMD to a surrounding blood pool.

2. The IMD of claim 1, wherein the retrieval feature comprises a tether ring, and the tether ring forms at least part of the ablating region.

3. The IMD of claim 1, further comprising a cutting feature disposed at or near the proximal end of the housing.

4. The IMD of claim 3, wherein the cutting feature is actuatable from a retracted position in which the cutting feature is disposed within the housing and an extended position in which at least a portion of the cutting feature extends and faces proximally.

5. The IMD of claim 3, wherein the cutting feature forms at least part of the ablating region.

6. The IMD of claim 1, wherein the power source has sufficient stored energy to provide sufficient energy to the ablating region of the retrieval feature to cause the ablating region to be heated sufficiently to ablate tissue proximate the retrieval feature.

7. The IMD of claim 1, further comprising an antenna operably coupled to the circuitry, the antenna configured to receive radiated energy directed towards the IMD from a location exterior to the patient and to provide the energy to the circuitry, and wherein the circuitry is configured to direct at least some of the energy to the power source and ultimately to the ablating region.

8. The IMD of claim 7, wherein the radiated energy comprises ultrasound.

9. The IMD of claim 7, wherein the radiated energy comprises RF energy.

10. The IMD of claim 1, wherein the IMD comprises a leadless cardiac pacemaker (LCP).

11. An implantable medical device (IMD) configured for deployment within a patient, the IMD comprising:
- a housing configured to be implantable within the patient at an implantation site;
- a fixation element for fixing the IMD to the patient at the implantation site;
- a retrieval feature secured relative to the housing for facilitating retrieval of the IMD from the implantation site; and
- an extraction element secured relative to the housing, the extraction element configured to expose at least part of the retrieval feature from tissue overgrowth by ablating at least some of the tissue overgrowth.

12. The IMD of claim 11, wherein the extraction element is configured to expose at least part of the retrieval feature from tissue overgrowth by cutting at least some of the tissue overgrowth.

13. The IMD of claim 11, wherein the extraction element comprises a heating element that is selectively operatively coupled to a power source to ablate the at least some of the tissue overgrowth away from the retrieval feature.

14. The IMD of claim 13, wherein the heating element comprises one or more heating elements that extend along an outer surface of the housing.

15. The IMD of claim 13, wherein the heating element comprises one or more heating elements that extend along an outer surface of the housing in a spiral shape.

16. The IMD of claim 11, wherein the extraction element comprises an energy-absorbable material that is sufficiently heated by an incident energy beam emanating from exterior to the patient to ablate or cut tissue overgrowth adjacent the extraction element.

17. An implantable medical device (IMD) configured for deployment within a patient, the IMD comprising:
- a housing configured to be implantable within the patient at an implantation site;
- a fixation element for fixing the IMD to the patient at the implantation site;
- a retrieval feature secured relative to the housing for facilitating retrieval of the IMD from the implantation site; and
- an extraction element secured relative to the housing, the extraction element comprising an energy-absorbable material that can be sufficiently heated by an incident energy beam emanating from exterior to the patient to ablate or cut tissue overgrowth adjacent the extraction element.

* * * * *